United States Patent [19]

Bush

[11] Patent Number: 4,822,610

[45] Date of Patent: Apr. 18, 1989

[54] METHOD FOR THE TREATMENT OF UROLOGIC DISORDERS

[76] Inventor: Irving M. Bush, Box 365, Burlington, Ill. 60109

[21] Appl. No.: 89,539

[22] Filed: Aug. 26, 1987

Related U.S. Application Data

[63] Continuation-in-part of Ser. No. 928,313, Nov. 7, 1986, abandoned.

[51] Int. Cl.$^4$ .................... A61K 33/30; A61K 31/075
[52] U.S. Cl. ..................................... 424/145; 514/718
[58] Field of Search ......................... 514/718; 424/145

[56] References Cited

U.S. PATENT DOCUMENTS 3,314,852  4/1967  Green et al. ......................... 514/718
3,549,766  12/1970  Berger et al. ....................... 514/718

FOREIGN PATENT DOCUMENTS 55313    7/1982  European Pat. Off. ............ 514/718
2305940  8/1973  Fed. Rep. of Germany ...... 514/718

Primary Examiner—Jerome D. Goldberg
Attorney, Agent, or Firm—Edward W. Osann, Jr.

[57] ABSTRACT

A novel method for the treatment of prostatitis, seminal vesiculitis, benign prostatic hypertrophy, prostatic abscess, bladder neck hypertrophy, urinary tract infection including urethritis and decreased liquification of semen by administering a pharmaceutically acceptable dosage of guaifenesin, or guaifenesin including zinc sulfate.

7 Claims, No Drawings

METHOD FOR THE TREATMENT OF UROLOGIC DISORDERS

This application is a continuation-in-part of my co-pending U.S. patent application Ser. No. 928,313, filed Nov. 7, 1986, now abandoned.

BACKGROUND OF THE INVENTION

The present invention relates to a novel method for the treatment of the urologic conditions known as prostatitis (P), seminal vesiculitis (SV), benign prostatic hypertrophy (BPH), prostatic abscess (PA), bladder neck hypertrophy (BNH), urinary tract infection (UTI) including urethritis and decreased liquification of semen (DLS).

These diseases of the urinary and genital tract of males and females are among the most common diseases (8%) seen in medical practice. They are often recurring, debilitating or persistent and take a great toll in patient morbidity. Many of the symptoms associated with P, SV, BPH, PA, BNH, UTI and DLS are related to the inability of associated organs to drain their mucoid or mucopurulent secretions which may or may not contain bacteria that are often resistent to many antibiotics. This inability to drain has been solved at the present time only through painful massage by the treating physician.

Guaifenesin $C_{10}H_{14}O_4$,2 - Propanediol, 3 (2 methoxyphenoxyl)-3-(o - Methoxyphenoxyl)-1,2-propanediol has in the past and at present been used as an expectorant. By increasing respiratory tract fluid (mucus) guaifenesin reportedly reduces the viscosity of tenacious secretions leading to removal of the offending material. Guaifenesin may also reduce respiratory tract adhesiveness and surface tension promoting ciliary action. It therefore has been used in the management of coughs associated with the common cold, bronchitis, laryngitis, pharyngitis, pertussis, influenza, measles and chronic paranasal sinusitis, all of which are diseases of the upper respiratory tract.

Mucolytic cough medications such as Robitussin (active ingredient guaifenesin) have been used to liquify cervical secretions in infertility problems on and off for many years. In 1980 we utilized Rubitussin to liquify viscid semen in infertility problems, but some of the patients complained about the effect of the alcohol. In early 1983 a patient with a chronic prostatic abscess was given guaifenesin by capsule (without alcohol) to encourage drainage of the thick purulent material normally expressed by vigorous prostatic massage once a week. Two phenomena occurred over the next 4 months. The secretions became slightly thinner and massage needed to be performed only once a month, as his prostate seemed distinctly smaller by rectal examination. In addition, there was no alcohol effect on the prostate.

This led to a prospective study of 158 patients with male infertility, prostatitis, seminal vesiculitis, prostatic abscess, benign prostatic hypertrophy and urinary tract infection. The men were given 400 to 600mg of guaifenesin for 2 to 14 months. Results included a decrease in: (a) semen viscosity; (b) white blood cell count, pH, bacterial content of ejaculated semen, an increase in semen zinc content and semen antibacterial factors as tested against known bacterial strains and (c) sperm mobility. Two unexpected findings were: 1. The reduction, in some patients, of their sperm counts; and 2. A decrease in prostatic size in selected long-term patients as measured by rectal exam, voiding studies, residual bladder urine and bladder and prostatic ultrasound. Side effects in these patients included rash, chronic cough, initial increased dysuria, constipation, sleeplessness and gastric upset. Further studies indicate that certain of these patients could tolerate the drug at 50 milligrams per day with similar results over a longer period of treatment.

The effect of concurrent zinc therapy (5–30mg of zinc sulfate per day) in a significant number of these patients was beneficial.

SUMMARY OF THE INVENTION

In accordance with the present invention, it has now surprisingly been found that guaifenesin with and without zinc is of use for the treatment of prostatitis (P), seminal vesiculitis (SV), benign prostatic hypertrophy (BPH), prostatic abscess (PA), bladder neck hypertrophy (BNH), urinary tract infection (UTI) including urethritis, and decreased liquification of semen (DLS). This use in the treatment of P, SV, BPH, PA, BNH, UTI and DLS has not been previously suggested and has not been reported. The object of the treatment is to encourage the drainage of the byproducts of infections and inflammations of the associated organ glands by increasing prostate, seminal vesicle, bladder neck, and urethral fluid secretion, and to reduce surface tension and adhesiveness of the mucosal lining of the prostate, seminal vesicle, bladder neck and urethra in males, and bladder neck and urethra in females. Testing of 30 patients with other mucolytic agents, including iodonated products, has not been effective.

DETAILED DESCRIPTION OF PREFERRED EMBODIMENT

Guaifenesin occurs as a white to slightly grey crystalline powder, having a bitter taste. Guaifenesin may have a slight characteristic odor. The powder tends to become lumpy on storage. It is soluble in alcohol and in water. It is also known as glyceryl guaiacolate or a-Glyceryl Guaracol Ether and is not a natural product, being manufactured by a chemical process. Its formula is Guaifenesin $C_{10}H_{14}O_4$ [198.22]1.2 - Propanediol, 3-(2-methoxyphenoxy)-3-(o Methoxyphenoxy)-1,2-propanediol. The drug can be identified by several chemical methods. It melts between 78° to 82° F. and has a pH between 5.0 and 7.0 in a solution of 1 to 100.

In treating patients with P, SV, BPH, PA, BNH, UTI and DLS, guaifenesin may, for example, be given 50–200mg once a day for 3 days, then twice a day for one week, then 150–1200mg a day in divided doses (three to six capsules). It can be administered by syrup but in the above conditions is preferred to be administered by 50mg to 200mg tablets for capsules. When produced with 5–30mg of zinc sulfate it is best provided by capsule.

It would be administered for 2 weeks in acute problems; up to 3 months in recurring problems; and up to one year in chronic problems. Prophylactic use would be employed in long term patients. This would include certain patients with low tolerance for guaifenesin but who could tolerate a 50mg per day dosage over a long period of time.

If the agent acts by lysing thick prostatic and seminal vesicle secretions, one would expect that theoretically trapped bacteria would "pour" forth and cause increased dysuria and frequency in patients with prostatic and seminal vesicle infections. This in fact does occur in at least one-third of the patients to some degree and most patients should be covered by antibacterial agents initially. This is also seen in women with elevated bladder necks given this agent.

At times the dysuria and frequency in certain patients may be so severe that the medication has to be abandoned. In some patients, stopping the medication has caused a gradual return to pre-treatment symptoms and findings. Significant reduction of sperm counts in males in the reproductive age would also necessitate the stopping of medication.

I claim as my invention:

1. A method for the treatment of the urologic conditions selected from the group consisting of prostatitis, seminal vesiculitis, benign prostatic hypertrophy, prostatic abscess, bladder neck hypertrophy, urinary tract infection including urethritis and decreased liquification of semen, which comprises administering orally to the patient in need of said treatment a pharmaceutically acceptable dosage of 50-1200mg of guaifenesin.

2. A method according to claim 1 wherein the dosage incorporates 5-30mg of pharmaceutically acceptable zinc sulfate.

3. A method according to claim 1 wherein the active agent guaifenesin is administered in a dosage not exceeding 50 mg per day in patients who have a relatively low tolerance to said agent.

4. A method for the treatment of the urologic conditions selected from the group consisting of prostatitis, seminal vesiculitis, benign prostatic hypertrophy, prostatic abscess, bladder neck hypertrophy, urinary tract infection including urethritis and decreased liquification of semen, which comprises administering orally to the patient in need of said treatment a pharmaceutically acceptable dosage of guaifenesin, wherein the active agent is administered in a dosage of 50-200mg once per day for 3 days, then twice a day for one week, and then 150-1200mg a day in divided dosages.

5. The method according to claim 4 wherein the dosage incorporates 5-30mg of pharmaceutically acceptable zinc sulfate.

6. A method according to claim 4 wherein said active agent is administered for 2 weeks in acute problems, up to 3 months in recurring problems, and up to one year in chronic problems.

7. A pharmaceutical composition capable of being orally administered and useful for treating the urological conditions selected from the group known as prostatitis, seminal vesiculitis, benign prostatic hypertrophy, prostatic abscess, bladder neck hypertrophy, urinary tract infection including urethritis and decreased liquification of semen, which comprises 50-1200 mg of pharmaceutically acceptable guaifenesin and 5-30mg of pharmaceutically acceptable zinc sulfate.

* * * * *